US00PP36271P2

(12) United States Plant Patent
Jandrew

(10) Patent No.: US PP36,271 P2
(45) Date of Patent: Nov. 26, 2024

(54) ***PETCHOA* PLANT NAMED 'Balpetcel145'**

(50) Latin Name: ***Petchoa,* Petunia-*Calibrachoa* *intergeneric* hybrid**
Varietal Denomination: Balpetcel145

(71) Applicant: Ball Horticultural Company, West Chicago, IL (US)

(72) Inventor: Jason Jandrew, Nipomo, CA (US)

(73) Assignee: BALL HORTICULTURAL COMPANY, West Chicago, IL (US)

( * ) Notice: Subject to any disclaimer, the term of this patent is extended or adjusted under 35 U.S.C. 154(b) by 0 days.

(21) Appl. No.: 18/628,441

(22) Filed: Apr. 5, 2024

(51) Int. Cl.
*A01H 6/00* (2018.01)
*A01H 5/02* (2018.01)

(52) U.S. Cl.
USPC ..... Plt./356.11

(58) Field of Classification Search
USPC ..... Plt./356.11
CPC ..... A01H 6/00; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Petchoa* plant named 'Balpetcel145', characterized by its dark yellow-colored flowers, medium green-colored foliage, and moderately vigorous, mounded-trailing growth habit, is disclosed.

1 Drawing Sheet

Latin name of genus and species of plant claimed: *Petchoa*, Petunia-*Calibrachoa* intergeneric hybrid.
Variety denomination: 'Balpetcel145'.

BACKGROUND OF THE INVENTION

The present invention relates to a new and distinct cultivar of *Petchoa* plant botanically known as *Petchoa*, Petunia-*Calibrachoa* intergeneric hybrid and hereinafter referred to by the cultivar name 'Balpetcel145'.

The new cultivar originated in a controlled breeding program in Guadalupe, California during March 2020. The objective of the breeding program was the development of *Petchoa* cultivars that have dark yellow-colored flowers and a mounded-trailing growth habit.

The new *Petchoa* cultivar is the result of cross-pollination. The female (seed) parent of the new cultivar is the proprietary *Petchoa* breeding selection coded 20-153-1, not patented, characterized by its single-type, light yellow-colored flowers, medium green-colored foliage, and moderately vigorous, mounded growth habit. The male (pollen) parent of the new cultivar is the proprietary *Petchoa* breeding selection coded 20-184-1, not patented, characterized by its single-type, dark yellow-colored flowers, medium green-colored foliage, low growth vigor, and mounded growth habit. The new cultivar was selected as a single flowering plant within the progeny of the above stated cross-pollination during September 2020 in a controlled environment in Guadalupe, California.

Asexual reproduction of the new cultivar by terminal stem cuttings since September 2020 in Guadalupe, California and West Chicago, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balpetcel145' as a new and distinct cultivar of *Petchoa* plant:

1. Dark yellow-colored flowers;
2. Medium green-colored foliage; and
3. Moderately vigorous, mounded-trailing growth habit.

Plants of the new cultivar differ from plants of the female parent primarily in having darker yellow-colored flowers. Plants of the new cultivar differ from plants of the male parent primarily in having more branches per plant and increased growth vigor.

Of the many commercially available *Petchoa* cultivars, the most similar in comparison to the new cultivar is Bee's Knees 'Balcobees', U.S. Plant Pat. No. 32,448. However, in comparison, plants of the new cultivar differ from plants of 'Balcobees' in at least the following characteristics:

1. Plants of the new cultivar have darker yellow-colored flowers than plants of 'Balcobees';
2. Plants of the new cultivar have a more mounded growth habit than plants of 'Balcobees'; and
3. Plants of the new cultivar have larger diameter corollas than plants of 'Balcobees'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balpetcel145'. The approximately 4-month-old plants were grown in 12-inch hanging baskets for approximately 8 weeks in an outdoor nursery in West Chicago, Ill. Treatments are described below in the Detailed Botanical Description.

DETAILED BOTANICAL DESCRIPTION

Figure 1:
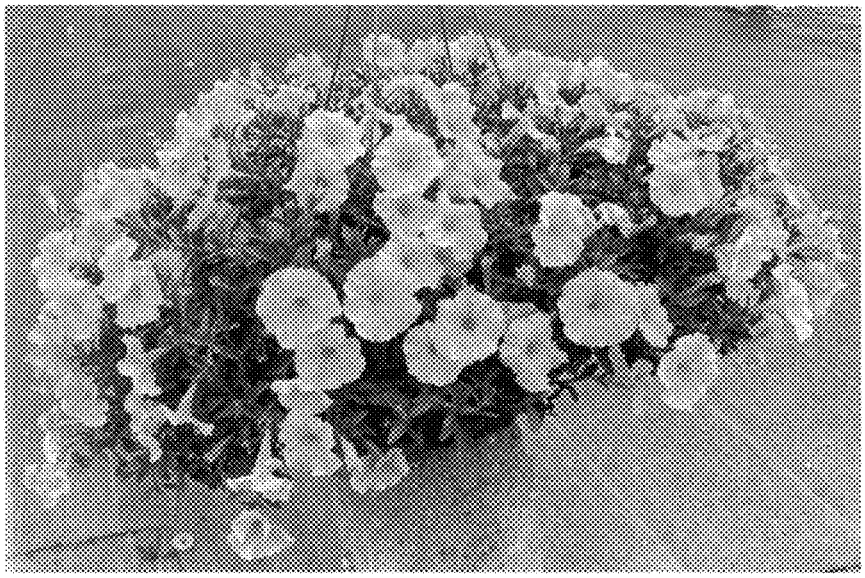
FIG. 1 illustrates a side view of the overall growth and flowering habit of 'Balpetcel145'.
Figure 2:
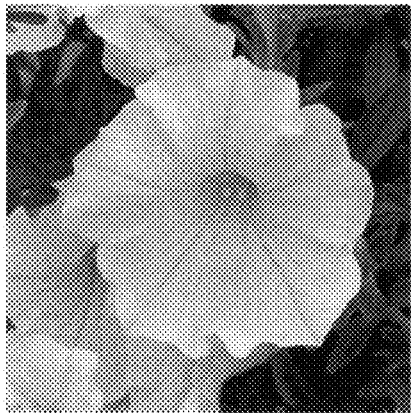
FIG. 2 illustrates a close-up view of an individual flower of 'Balpetcel145'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2023 under natural light conditions in West Chicago, Ill.

The following descriptions and measurements describe approximately 4-month-old plants produced from cuttings from stock plants and grown under conditions comparable to those used in commercial practice. The plants were grown in 12-inch hanging baskets utilizing a soilless growth medium for approximately 8 weeks in an outdoor nursery in West Chicago, Ill. Plants were given three pinches prior to transplant. Eight weeks after cuttings were stuck, plants were sprayed with growth regulators B-NINE (daminozide[butanedioic acid mono (2,2-dimethylhydrazide)]) at 2,500 ppm and CYCOCEL (chlormequat (2-chloroethyl)trimethylammonium chloride) at 800 ppm. Prior to transplant plants were grown in a polycarbonate greenhouse in West Chicago, Ill. Greenhouse temperatures were maintained at approximately 75° F. to 80° F. (24° C. to 27° C.) during the day and approximately 65° F. to 70° F. (18° C. to 21° C.) during the night. Supplemental lighting was used during propagation stage. Measurements and numerical values represent averages of typical plants.

Botanical classification: *Petchoa*, Petunia-*Calibrachoa* intergeneric hybrid, 'Balpetcel145'.

Parentage:

*Female parent*.—Proprietary *Petchoa* breeding selection coded 20-153-1, not patented.

*Male parent*.—Proprietary *Petchoa* breeding selection coded 20-184-1, not patented.

Propagation:

*Type cutting*.—Terminal stem.

*Time to initiate roots*.—Approximately 6 to 9 days.

*Time to produce a rooted cutting*.—Approximately 21 to 28 days.

*Root description*.—Fibrous.

*Rooting habit*.—Freely branching.

Plant description:

*Commercial crop time*.—Approximately 6 to 8 weeks from a rooted cutting to finish in a 10 cm pot.

*Growth habit and general appearance*.—Moderately vigorous, mounded-trailing growth habit.

*Size*.—Height from soil level to top of plant plane: Approximately 18.5 cm. Width: Approximately 72.0 cm.

*Branching habit*.—Freely branching. Pinching enhances basal branching. Quantity of main branches per plant: Approximately 5.

*Lateral branch*.—Strength: Moderate. Length: Approximately 29.0 cm. Diameter: Approximately 4.0 mm. Length of central internode: Approximately 2.2 cm. Texture: Densely glandular pubescent with a mixture of long and short hairs. Gland color: Colorless, transparent. Color of young stems: 144A. Color of mature stems: 146C.

Foliage description:

*General description*.—Quantity of leaves per main branch: Approximately 16. Fragrance: Slight. Form: Simple. Arrangement on flowering stem: Opposite.

*Leaves*.—Aspect: Acute angle to perpendicular to stem. Shape: Elliptic to ovate. Margin: Entire. Apex: Acute. Base: Broadly attenuate. Venation pattern: Pinnate. Length of mature leaf: Approximately 4.3 cm. Width of mature leaf: Approximately 1.8 cm. Texture of upper and lower surfaces: Moderately glandular pubescent. Gland color: Colorless, transparent. Color of upper surface of young and mature foliage: 137A with venation of 146C to indistinguishable. Color of lower surface of young and mature foliage: Closest to 146B with venation of 146D to indistinguishable.

*Petiole*.—Length: Approximately 4.0 mm. Width: Approximately 3.0 mm. Texture: Densely glandular pubescent with a mixture of long and short hairs. Gland color: Colorless, transparent. Color: 146D.

Flowering description:

*Flowering habit*.—'Balpetcel145' is freely flowering under outdoor growing conditions with substantially continuous blooming from spring through autumn and year-round in greenhouse environment.

*Lastingness of individual flower on the plant*.—Approximately 10 to 12 days.

Flower description:

*General description*.—Type: Simple, salverform. Quantity per plant: Approximately 60. Fragrance: None detected.

*Bud*.—Rate of opening: Generally takes 3 to 5 days for bud to progress from first color to fully open flower. Quantity per plant: Approximately 34.

*Bud just before opening*.—Shape: Obovoid. Length: Approximately 3.5 cm. Diameter at apex: Approximately 1.5 cm. Diameter at base: Approximately 3.0 mm. Texture: Densely glandular pubescent. Gland color: Colorless, transparent. Color of petal portion: 1A with venation of 144A.

*Corolla*.—Diameter: Approximately 6.0 cm.

*Petals*.—Quantity: Approximately 5, fused to form a tube. Shape: Obovate. Appearance: Matte. Margin: Entire, ruffled. Apex: Cuspidate. Length from throat: Approximately 2.5 cm. Width: Approximately 3.3 cm. Length of free portion: Approximately 1.1 cm. Texture of upper surface: Glabrous. Texture of lower surface: Sparsely glandular pubescent. Gland color: Colorless, transparent. Color of upper surface when first and fully open: 6A to 6B at throat opening transitioning through 6C to 6D at outer margins, weak midveins of 144A. Color of lower surface when first and fully open: 6C to 6D with medium midveins of 144A.

*Corolla tube*.—Length: Approximately 3.0 cm. Diameter at distal end: Approximately 1.1 cm. Diameter at proximal end: Approximately 3.0 mm. Texture of inner surface: Glabrous. Texture of outer surface: Densely glandular pubescent. Gland color: Colorless, transparent. Color of inner surface: Closest to 12A with base of 145C, venation of 144C. Color of outer surface: Closest to 6C with venation of 144A.

*Corolla*.—Length: Approximately 1.5 cm. Width: Approximately 1.4 cm.

*Sepals*.—Quantity per flower: 5, fused at base. Shape: Linear. Margin: Entire. Apex: Broadly acute. Length: Approximately 1.5 cm. Width: Approximately 2.0 mm to 3.0 mm. Texture of upper and lower surfaces: Densely glandular pubescent. Gland color: Colorless, transparent. Color of upper surface: 137A. Color of lower surface: 138A with 144A at base.

*Peduncle*.—Strength: Strong, flexible. Aspect: Acute angle to stem. Length: Approximately 2.0 cm. Diameter: Approximately 2.0 mm. Texture: Densely pubescent with a mixture of long and short glandular hairs. Gland color: Colorless, transparent. Color: 144A.

*Reproductive organs*.—Androecium: Stamen quantity: Typically 5 and rarely up to 7, basifixed. Stamen length: Approximately 2.2 cm to 2.7 cm. Filament length of fixed portion: Approximately 1.3 cm. Filament color: 155A with an overlay of 144A near anther. Anther shape: Bilobed. Anther length: Approximately 2.0 mm. Anther color: 4D. Pollen amount: Abundant. Pollen color: 155A. Gynoecium: Pistil quantity: 1 per flower. Pistil length: Approximately 2.5 cm. Stigma shape: Funnel. Stigma length: Approximately 1.0 mm. Stigma color: 144A. Style length: Approximately 2.0 cm. Style color: 145D. Ovary length: Approximately 4.0 mm. Ovary color: 144A.

Seed and fruit production: Neither seed nor fruit production has been observed.

Disease and pest resistance: Resistance to pathogens and pests common to *Petchoa* has not been observed.

What is claimed is:

1. A new and distinct cultivar of *Petchoa*, Petunia-*Calibrachoa* intergeneric hybrid plant named 'Balpetcel145', substantially as herein illustrated and described.

* * * * *